(12) United States Patent
Cook et al.

(10) Patent No.: US 7,871,659 B2
(45) Date of Patent: Jan. 18, 2011

(54) METHOD OF VISUALIZING MEDICAL DEVICES DURING IMPLANTATION

(75) Inventors: Alonzo D. Cook, Flagstaff, AZ (US);
Warren J. Cutright, Flagstaff, AZ (US);
Robert C. Krall, Flagstaff, AZ (US);
William D. Montgomery, Flagstaff, AZ (US)

(73) Assignee: Gore Enterprise Holdings, Inc., Newark, DE (US)

( * ) Notice: Subject to any disclaimer, the term of this patent is extended or adjusted under 35 U.S.C. 154(b) by 0 days.

(21) Appl. No.: 12/106,064

(22) Filed: Apr. 18, 2008

(65) Prior Publication Data

US 2008/0213463 A1 Sep. 4, 2008

Related U.S. Application Data

(60) Division of application No. 11/051,299, filed on Feb. 4, 2005, now abandoned, which is a continuation of application No. 10/159,836, filed on May 31, 2002, now abandoned.

(51) Int. Cl.
*B05D 3/00* (2006.01)
*A61B 8/00* (2006.01)

(52) U.S. Cl. .............. 427/2.1; 427/2.24; 427/2.25; 427/407.1; 427/412.3; 427/412.4; 600/437

(58) Field of Classification Search .......... 427/2.1, 427/2.24, 2.25, 407.1, 412.2, 412.4, 412.3; 600/437
See application file for complete search history.

(56) References Cited

U.S. PATENT DOCUMENTS

| | | | |
|---|---|---|---|
| 3,739,770 A | 6/1973 | Mori | |
| 3,907,675 A * | 9/1975 | Chapurlat et al. | 210/654 |
| 3,939,849 A * | 2/1976 | Baxter et al. | 131/332 |
| 4,038,365 A * | 7/1977 | Patil et al. | 423/161 |
| 4,113,912 A | 9/1978 | Okita | |
| 4,193,138 A | 3/1980 | Okita | |
| 4,525,374 A | 6/1985 | Vaillancourt | |
| 4,917,793 A | 4/1990 | Pitt et al. | |
| 5,041,225 A | 8/1991 | Norman | |
| 5,049,275 A * | 9/1991 | Gillberg-LaForce et al. | 210/500.27 |
| 5,090,422 A | 2/1992 | Dahl et al. | |
| 5,443,727 A | 8/1995 | Gagnon | |
| 5,562,728 A | 10/1996 | Lazarus et al. | |
| 5,571,169 A | 11/1996 | Plaia et al. | |
| 5,575,816 A | 11/1996 | Rudnick et al. | |
| 5,662,701 A | 9/1997 | Plaia et al. | |
| 5,749,880 A | 5/1998 | Banas et al. | |
| 5,755,762 A | 5/1998 | Bush | |
| 5,769,882 A | 6/1998 | Fogarty et al. | |
| 5,782,847 A | 7/1998 | Plaia et al. | |
| 5,799,384 A | 9/1998 | Schwartz et al. | |
| 5,865,844 A | 2/1999 | Plaia et al. | |
| 5,873,905 A | 2/1999 | Plaia et al. | |
| 5,879,366 A | 3/1999 | Shaw et al. | |
| 5,897,955 A | 4/1999 | Drumheller | |
| 5,902,745 A | 5/1999 | Butler et al. | |
| 5,906,639 A | 5/1999 | Rudnick et al. | |
| 6,053,939 A | 4/2000 | Okuda et al. | |
| 6,080,182 A | 6/2000 | Shaw et al. | |
| 6,171,329 B1 | 1/2001 | Shaw et al. | |
| 6,174,322 B1 | 1/2001 | Schneidt | |
| 6,623,508 B2 | 9/2003 | Shaw et al. | |

FOREIGN PATENT DOCUMENTS

| | | | |
|---|---|---|---|
| JP | 10-244611 A | * | 9/1998 |
| JP | 10244611 | | 9/1998 |
| WO | 9640305 | | 12/1996 |

* cited by examiner

*Primary Examiner*—William Phillip Fletcher, III
(74) *Attorney, Agent, or Firm*—Eric J. Sheets; David J. Johns

(57) ABSTRACT

A method of rapid visualization of an implantable medical device using technology for viewing inside of a mammalian body. These technologies include ultrasound echocardiography and video imaging such as that used during laparoscopic procedures.

8 Claims, 6 Drawing Sheets

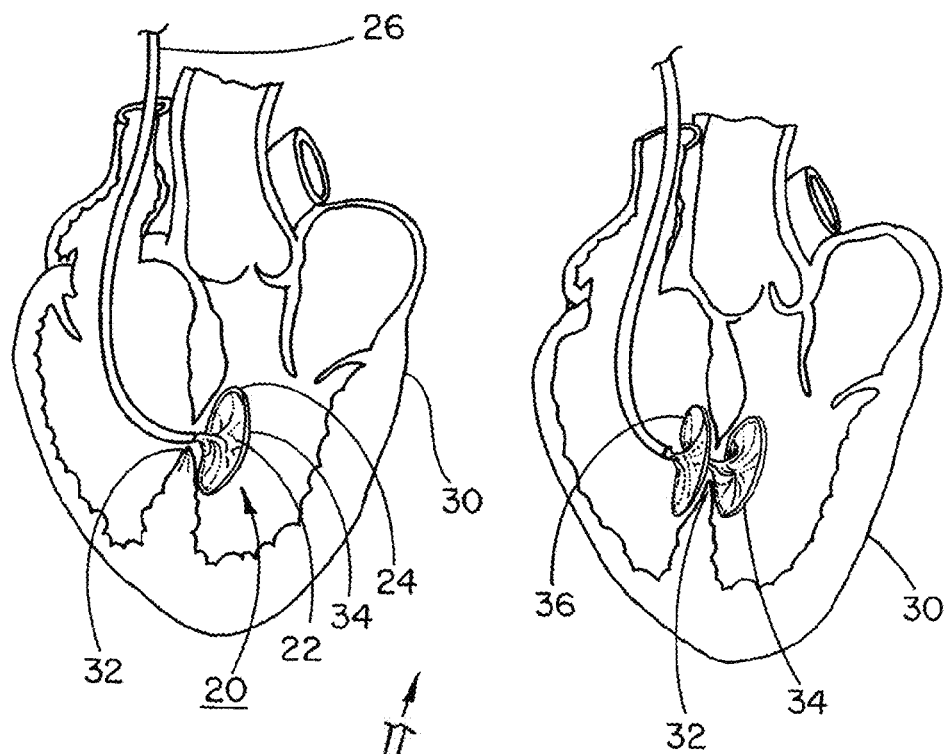
FIG. 2
FIG. 3
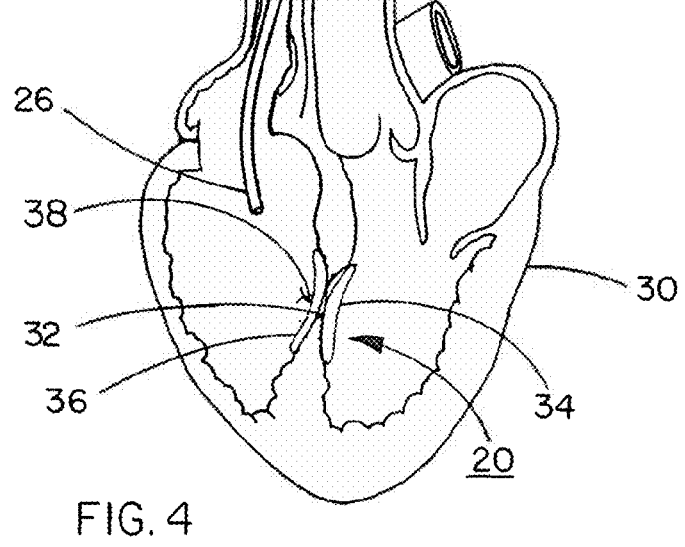
FIG. 4

METHOD OF VISUALIZING MEDICAL DEVICES DURING IMPLANTATION

CROSS REFERENCE TO RELATED APPLICATIONS

This application is a divisional of U.S. patent application Ser. No. 11/051,299 filed Feb. 4, 2005, now abandoned which is a continuation of U.S. patent application Ser. No. 10/159,836 filed May 31, 2002 now abandoned.

BACKGROUND OF THE INVENTION

1. Field of the Invention

The present invention relates to implantable medical devices and more particularly to medical devices that are designed to be surgically or endoluminally placed in a body.

2. Description of Related Art

Medical devices designed to be introduced through catheter-based delivery systems or through trocars are often deployed using various remote visualization techniques, such as x-ray imaging, fluoroscopy, ultrasound, and/or video imaging.

It has been determined that devices made from certain microporous polymers, such as expanded polytetrafluoroethylene (PTFE), sometimes are difficult to properly visualize using certain remote visualization techniques because air trapped in the microporous polymer can distort remote images. Most porous materials will eventually wet-out with body fluids following implantation, although this process may take time. In the case of expanded PTFE, its hydrophobic nature can vastly slow the process of replacing air with fluid following implantation—which can lead to poor initial visualization following implantation.

Expanded PTFE is now a preferred material for use with many implantable surgical and interventional devices, such as vascular grafts, implantable sheet materials, stent-grafts, embolic filters, and various occluders including septal occluders. As use of this material has increased, it has become evident that these devices often do not provide optimal initial visual clarity under ultrasound, video imaging, and direct visualization.

Ultrasonic imaging is a somewhat vexing problem for implantable porous materials. "Sound" is generally defined as a periodic disturbance in fluid density, or inelastic strain of a solid, generated by a vibrating object. In the case of "ultrasound," it is generally defined as sound with a frequency of over about 20,000 Hz. The velocity of ultrasound waves depends on the medium through which they propagate. The velocity of sound through air is about 330 m/sec; the velocity of sound through water is about 1480 m/sec; the velocity of sound through muscle is about 1580 m/sec. While liquids tend to transmit ultrasound waves, air tends to absorb such waves. As a result, the presence of air in an implantable membrane introduces a disruptive layer that will interfere with normal ultrasound wave transmission. While it is recognized that these problems can be corrected by replacing the air in the porous material with liquid, this process has generally been addressed through the slow wetting-out of the porous material over time following implantation.

For some applications, this process of slow wetting-out may be undesirable. With the growing advent of remotely delivered devices, more and more comprising a membrane attached to an expanding frame, there is a need for instantaneous exact visualization of the device prior to and immediately following implantation. Devices such as fluoroscopes and x-rays can provide such visualization, but the harmful radiation these devices deliver to patients and medical personnel make them less desirable for daily use. Due to its very low side-effect risks, ultrasound visualization would be a preferred method of visualization, but only if the remotely deployed devices can be instantly visualized without interference. To date, no entirely suitable method of instantly ultrasonically visualizing a device incorporating a porous membrane has yet been developed.

Visualization and wet-out issues are discussed in a number of existing patents. For instance, in Japanese Patent 10-244611 to Oga it is recognized that expanded PTFE implantable sheet material has a number of problems, including that: it cannot be seen through; it reflects light, causing glare problems for surgical staff; and it cannot be effectively probed with ultrasound. The patent teaches that these problems can be corrected by providing an expanded PTFE center layer that is pre-impregnated with an aqueous liquid and two outer layers sealing the liquid impregnated layer. Liquid polyvinyl alcohol (PVA) may be included in the liquid impregnated layer. While this approach may solve visualization problems, it presents a number of other problems, including vastly increased manufacturing, packaging, shipping, and handling problems while dealing with a pre-wetted material.

In PCT Patent Application WO 96/40305 to Hubbard, it is again recognized that expanded PTFE cannot be seen through, it reflects light, and it is not suitable for ultrasound imaging. Hubbard teaches that the expanded PTFE can be pre-impregnated with saline, polysaccharides, gums and gels, glycerol/gum xanthan, sera/lipids, or the like, and then shipped wet. Again, this concept requires increased expense and effort in dealing with the manufacturing, packaging, and handling of a "wet" product.

Separate from visualization issues, a number of other patents suggest incorporating wet or wettable materials within implantable devices for various reasons of improved device performance. For instance, U.S. Pat. No. 4,193,138 to Okita teaches use of an expanded PTFE vascular graft with a water-soluble polymer in its pores. The polymer in the pores forms a bonded film of water, preventing adsorption of plasma protein, which is claimed to improve patency. Multiple types of cross-linked PVA are disclosed as a "swollen gel" in the pores of the expanded PTFE.

Similarly, U.S. Pat. No. 5,041,225 to Norman teaches an expanded PTFE membrane coated with a combination of a hydrophilic polymer and a complexing agent. The polymer is rendered water insoluble by the complexing agent, which also provides good protein bonding. PVA is taught as the hydrophilic polymer and various inorganic compounds, such as boric acid, sodium borate, etc., are taught as the complexing agents.

In U.S. Pat. No. 5,049,275 to Gillberg-LaForce et al., it is taught that a micro-porous membrane, such as expanded PTFE, can be changed from hydrophobic to hydrophilic by incorporating a vinyl monomer, such as PVA, polymerized within the pores of the membrane. This patent teaches that the membrane should be rendered hydrophilic to be used as a separation membrane in rechargable batteries, or in blood oxygenators, in bioreactors or for use in blood dialysis, or to support a liquid membrane, wherein a liquid which is imbibed in the pores of the microporous membrane is the medium through which transport takes place.

In U.S. Pat. No. 4,525,374 to Vaillancourt it is taught that an expanded PTFE membrane can be coated to render it hydrophilic by treating it with triethanolamine dodecylbenzene sulfonate and then dried. The patent teaches that the membrane should be rendered hydrophilic to maintain the existing (inert characteristics) surface properties of hydrophobic membrane filters and yet render these filters hydrophilic such that they can be used for fluid filtration, particularly for pharmaceutical processes.

In U.S. Pat. No. 5,755,762 to Bush it is taught that electrical conductivity can be improved by treating an expanded PTFE jacketed pacing or defibrillation lead with a wet-out agent, such as DSS, TDMAC, surfactants, or hydrogels. Likewise in U.S. Pat. No. 5,090,422 to Dahl et al., it is taught that an expanded PTFE pacing lead jacket can be treated with a "wetting agent, or surface modified" to allow wet-out and improve initial electrical performance.

U.S. Pat. No. 5,897,955 to Drumheller et al. teaches that a PVA coating can be provided on an expanded PTFE surface to aid in attaching various biological entities. U.S. Pat. No. 5,902,745 to Butler et al. teaches that a PVA treatment can be provided in the wall of an expanded PTFE cell containment device to aid in seeing the cells inside.

In summary, numerous concepts have been previously proposed for rendering a porous membrane wet or wettable for a number of functional reasons. However, particularly with regard to endoscopically deployed devices that mount porous membranes on some form of support frame, none of these previous concepts has taught or suggested an ideal solution to aid in the instant visualization of an implanted device that is highly effective, simple to implement, and does not urden the manufacturing, packaging, shipping, or handling of the implantable device.

SUMMARY OF THE INVENTION

The present invention employs treatment of an implantable medical device, comprising a microporous membrane supported by a frame, that allows the device to be rapidly and accurately visualized by ultrasound and video imaging, and renders the device transparent under direct visualization. The present invention eliminates air-interference issues with porous membrane devices, such as those incorporating expanded PTFE, by modifying the porous membrane with a dried hydrophilic substance, such as polyvinyl alcohol (PVA), to allow the membrane to rapidly displace air with liquid once introduced into the body or otherwise contacted with an aqueous liquid. The presence of dried hydrophilic substance on and/or in the pores of the membrane vastly increases the rate at which air is displaced by aqueous liquids and improves the rapid and precise visualization of the device.

The preferred device of the present invention comprises an expandable frame attached to a porous expanded PTFE membrane that includes a cross-linked PVA material bound to the membrane. This construction is suitable for use with a wide variety of remotely deployed devices, such as septal and other occlusion devices, embolic filters, certain stent-graft devices, implantable sheets, and the like. In addition to allowing for very rapid accurate visualization of the implanted device, the present invention is believed to also provide a number of other benefits, including improved biological performance and better ingrowth.

Another benefit of the present invention is its ability to absorb aqueous solution, which may contribute to a significant decrease in the abrasion type injuries seen when membranes come in contact with tissue. In those instances where a membrane that is impervious to fluid transmission is required, a barrier membrane can be inserted between layers of expanded PTFE, thus allowing ultrasound transmission and ingrowth.

These and other benefits of the present invention will be appreciated from review of the following description.

DESCRIPTION OF THE DRAWINGS

The operation of the present invention should become apparent from the following description when considered in conjunction with the accompanying drawings, in which:

FIG. 2 is a cross-section view of a heart, including a septal defect therein, showing initial deployment of the septal defect closure device of FIG. 1;

FIG. 3 is a cross-section view of the heart showing second stage deployment of the septal defect closure device;

FIG. 4 is a cross-section view of the heart showing final deployment of the septal defect closure device;

DETAILED DESCRIPTION OF THE INVENTION

The present invention is directed to the modification of implantable devices that employ a porous membrane mounted on one or more frame elements so as to allow the device to be deployed remotely in a medical procedure. The porous membrane of the present invention is loaded with a hydrophilic substance that is dried on and/or within the membrane. In its pre-implanted state the device of the present invention is visually and tactilely indistinguishable from conventional membrane and frame devices, but when exposed to an aqueous liquid the membrane portion wets-out rapidly so that the device becomes translucent or transparent to light and ultrasonic imaging.

Figure 1:
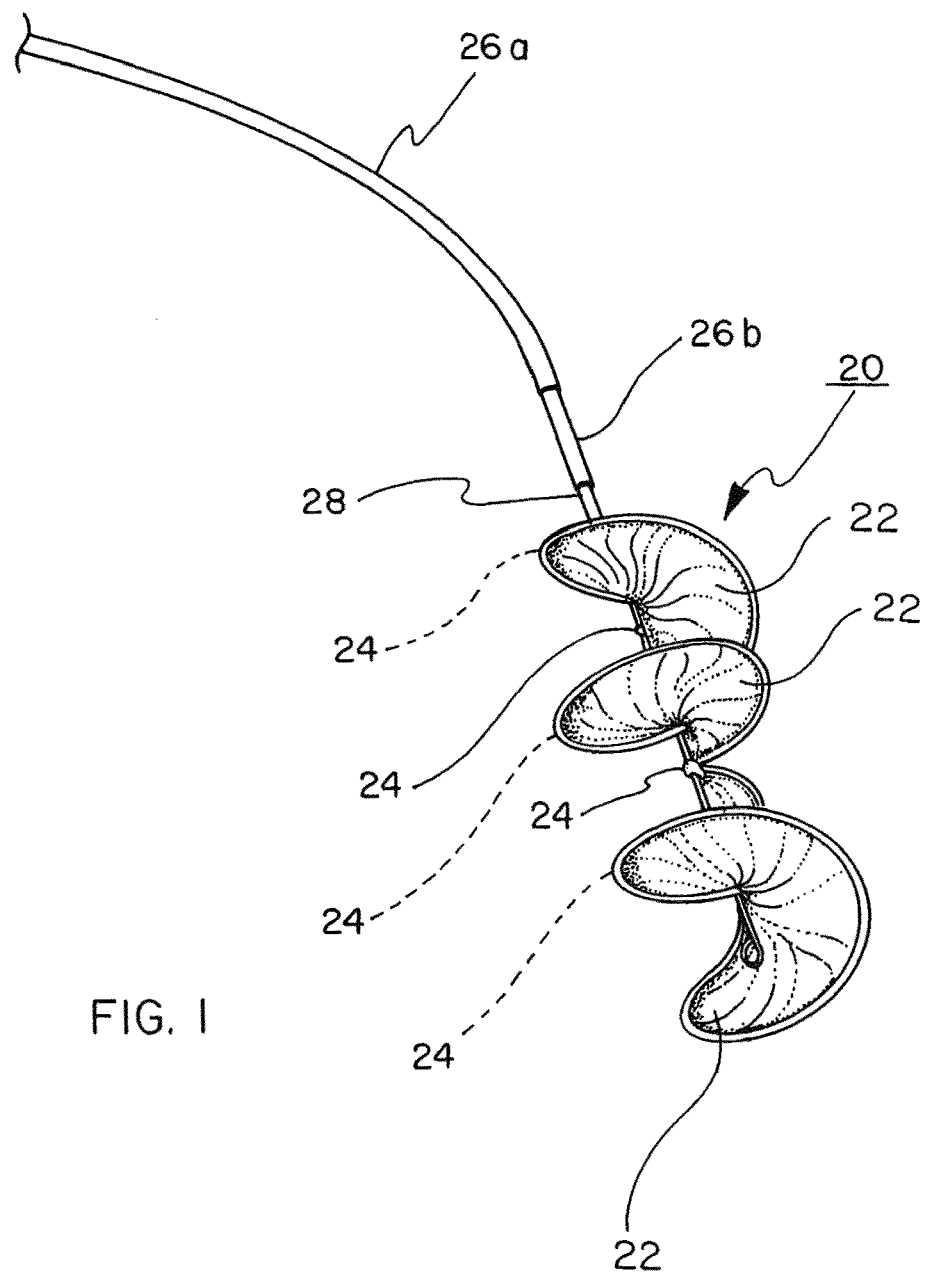
FIG. 1 is a three-quarter perspective view of a septal defect closure device of the present invention, including a frame and a porous membrane.

One embodiment of the present invention is illustrated in FIG. 1. In this embodiment, the device comprises a septal defect closure device 20 comprising a porous membrane 22 and a helical support frame 24. The device is delivered to a treatment site in a body using a series of concentrically mounted catheter tubes 26a and 26b mounted on a mandrel 28. This device is similar to those disclosed in U.S. Pat. Nos.

5,879,366, 6,080,182, and 6,171,329, all to Shaw et al., and currently available for investigational purposes from W. L. Gore & Associates, Inc., Flagstaff, Ariz., under the trademark HELEX™.

The device illustrated in FIG. 1 differs from the devices described in the Shaw patents and available under the HELEX trademark in that the membrane has been treated in accordance with the present invention to render it hydrophilic. When treated in the manner described in detail below, the septal defect closure device will rapidly absorb aqueous solution so as to become transparent upon introduction into the blood system of a patient. This modification provides a number of important benefits.

The process for deploying a septal defect closure device 20 of the present invention is illustrated in FIGS. 2 through 4. As shown, the defect closure device 20 is guided into a heart 30 using the catheter tube 26 so as to position the device through a septal defect 32. Shown in FIG. 2, a first portion 34 of the device is then deployed on one side of the septal defect 32 by releasing part of the frame 24 and attached membrane 22 from the catheter tube 26. A second portion 36 of the device is subsequently deployed on an opposite side of the septal defect, as is shown in FIG. 3. Once imaging assures the medical staff that the device is properly positioned, as is shown in FIG. 4, a final latch 38 is deployed to lock the device in the septal defect and the catheter tube 26 is removed.

Figure 5:
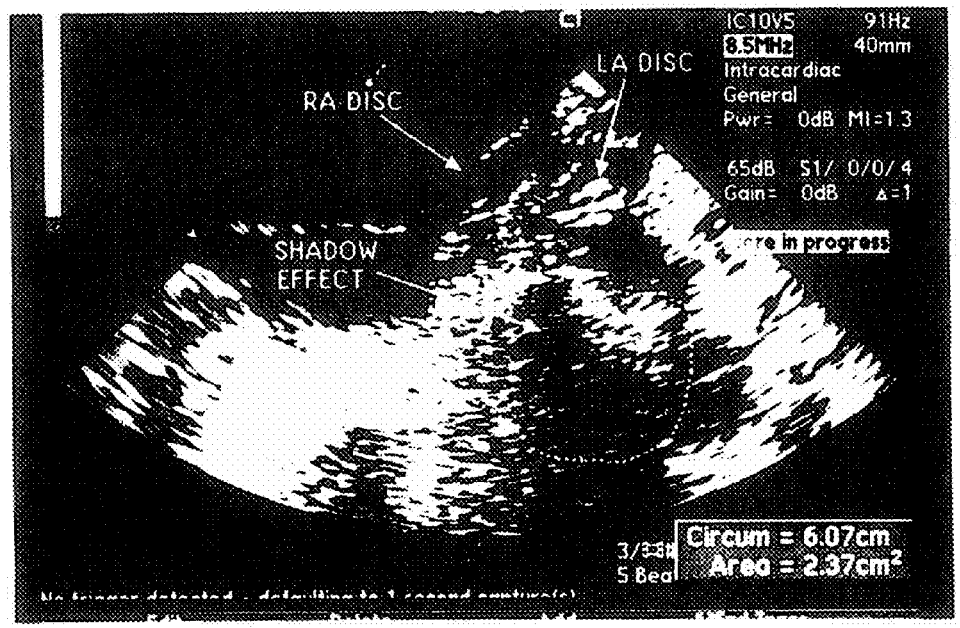
FIG. 5 is an ultrasound image of a heart having been sealed with a conventional septal defect closure device, including a "shadow effect" caused by air trapped in the membrane portion of the device.

Although the conventional device functions very well, its membrane component is constructed from a porous expanded polytetrafluoroethylene (PTFE) membrane, which is hydrophobic. As a result, the membrane may take many days or weeks to fully absorb surrounding solution and become visually and sonically transparent. FIG. 5 is an ultrasonic image of a conventional septal defect closure device shown immediately following implantation. The image shows a distinct shadow (marked "Shadow Effect") caused by air trapped in the membrane portion of the device. Until wet-out occurs, this shadow effect makes it difficult to determine the precise location of the device and the structure of surrounding tissue using ultrasonic imaging.

Figure 6:
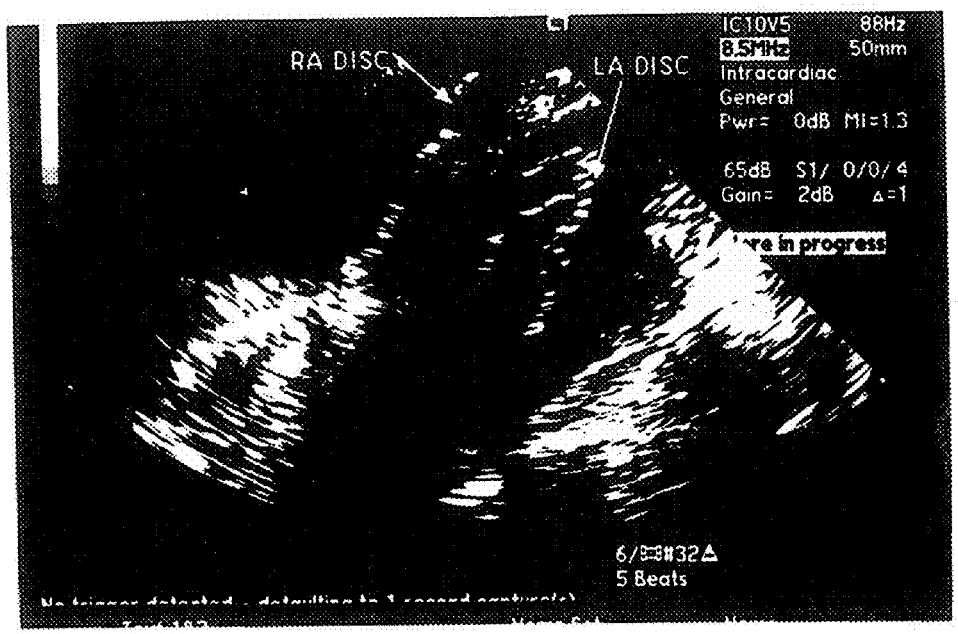
FIG. 6 is an ultrasound image of a heart having been sealed with a septal defect closure device of the present invention, illustrating no shadow effect.

FIG. 6 is an ultrasonic image of a device of the present invention of comparable orientation and dimensions of the device shown in FIG. 5. This device is shown as imaged by ultrasound immediately after implantation, but as can be seen, no shadow effect is evident in the image. This is because the provision of a dried hydrophilic substance within the pores of the membrane 22 causes the membrane to rapidly wet-out once exposed to an aqueous medium, such as blood. As a result, both the device and the surrounding tissues can be clearly viewed using ultrasonic imaging almost instantaneously following implantation.

As the terms "rapid" and "rapidly" are used to describe the wet-out process of the present invention, they mean that most if not all of the air normally trapped in the porous structure of the membrane has been displaced by liquid within 30 seconds following contact with an aqueous medium, and more preferably within 5 to 10 seconds following aqueous medium contact. The effective evacuation of air can be confirmed in a porous expanded PTFE material once the membrane becomes translucent to visual light.

To construct a device of the present invention, a hydrophilic layer is formed on a membrane by applying a polymeric hydrophilic surfactant, such as but not limited to polyvinyl alcohol (PVA) or polyvinyl pyrrolidone (PVP), to the surface of the membrane. The hydrophilic substance may then be bound in place, such as through cross-linking the surfactant to itself in situ. For a porous frame member, the hydrophilic layer may optionally be adsorbed within the porous void spaces of the frame member as well.

When using a hydrophobic membrane, and if the polymer chosen for the hydrophilic layer dissolves in only high surface tension solvents, the hydrophobic membrane should be pre-wetted with a miscible solvent having a low surface tension to enhance adsorption of the polymer onto the membrane. Examples of appropriate pre-wetting agents can be, but are not limited to, isopropyl alcohol (IPA), ethanol, or methanol in a concentration of about 25% to 100%, preferably 50% to 100%, and most preferably 70% to 100%. The membrane should be immersed in the miscible solvent for about 1 second to one hour, preferably 5 seconds to five minutes, and most preferably for about 30 to 60 seconds.

The membrane is then immediately transferred into a solution of the polymeric surfactant in an appropriate solvent. For example, a solution comprising a polymeric surfactant dissolved in a suitable solvent (such as water), at a concentration of about 0.001% to about 99.9%, preferably about 0.25% to about 5%, and most preferably 1.5% to 2.5%, is initially adsorbed onto the surfaces and optionally into the porous spaces of a porous membrane simply by dipping the membrane in the solution for about 0.05 minutes to about 24 hours, preferably 5 to 180 minutes, and most preferably for about 10 to 30 minutes. This treatment step permits physisorption of the surfactant to the surface of the membrane. The membrane is then rinsed to wash off any excess polymeric surfactant and then the polymeric surfactant may be cross-linked in place.

Suitable materials for the hydrophilic layer include, but are not limited to, polyvinyl alcohol, polyethylene glycol, polypropylene glycol, dextran, agarose, alginate, polyacrylamide, polyglycidol, poly(vinyl alcohol-co-ethylene), poly (ethyleneglycol-co-propyleneglycol), poly(vinyl acetate-co-vinyl alcohol), poly(tetrafluoroethylene co-vinyl alcohol), poly(acrylonitrile-co-acrylamide), poly (acrylonitrile-co-acrylic acid-co-acrylamide), polyacrylic acid, poly-lysine, polyethyleneimine, polyvinyl pyrrolidone, polyhydroxyethylmethacrylate, and polysulfone, and their copolymers, either alone or in combination.

Preferred copolymers for formation of the hydrophilic layer are copolymers comprising at least one moiety capable of physiochemically adsorbing to the membrane, at least one moiety capable of chemical modification with a suitable agent, and at least one moiety capable of interacting with high surface tension fluids. These moieties may be selected such that one moiety fulfills all of these three roles simultaneously, fulfills two roles, or fulfills only one role.

Suitable solvents for this purpose include, but are not limited to, methanol, ethanol, isopropanol, tetrahydrofuran, trifluoroacetic acid, acetone, water, dimethyl formamide (DMF), dimethyl sulfoxide (DMSO), acetonitrile, benzene, hexane, chloroform, and supercritical carbon dioxide.

The polymeric surfactant of the layer is covalently cross-linked to itself in situ using a suitable cross-linking agent to produce surface-bound planar molecules of extremely high molecular weight. These very high molecular weight molecules serve to greatly reduce or eliminate the potential for desorption or migration of the surfactant.

Suitable reagents for use in cross-linking the polymeric surfactant in situ are compounds comprising at least two chemically functional groups, either homofunctional or heterofunctional, that include, but are not limited to, aldehydes, epoxides, acyl halides, aryl halides, isocyanates, amines, anhydrides, acids, alcohols, haloacetals, arylcarbonates, thiols, esters, imides, vinyls, azides, nitros, peroxides, sulfones, and maleimides.

The reagents should be dissolved in solvents that wet the adsorbed layer. Solvents suitable for dissolving the cross-linking reagent include, but are not limited to, acetone, water, alcohols, tetrahydrofuran (THF), dimethyl sulfoxide (DMSO), dimethyl formamide (DMF), benzene, acetonitrile, and dioxane. Other possible reagents include, but are not limited to, free radicals, anions, cations, plasma irradiation, electron irradiation, and photon irradiation. One preferred cross-linking agent is glutaraldehyde, preferably using a catalyst of hydrochloric acid (HCl), preferably dissolved in water. The membrane with the surfactant is then submersed into a solution of, but not limited to, glutaraldehyde/HCl in a water concentration of about 0.001%/0.001% to 99.9%/99.9%, preferably 0.1%/0.1% to 5%/5%, and most preferably 1%/1% to 3%/3%. The membrane should be submersed for anywhere from 1 second to 3 hours, but preferably 1 minute to one hour, and most preferably 10 to 20 minutes followed by a final rinse to wash off any excess glutaraldehyde/HCl uncrosslinked residual.

When treated in this manner, the membrane will rapidly absorb liquid and will render the device translucent to light and relatively transparent to sound. As such, the present invention has numerous applications for all kinds of endoluminally and surgically delivered devices, including: implantable closure devices; implantable filter devices; various graft and stent-graft devices; various implantable sheets, including sheets that include support frames; implantable devices with impermeable barrier layers, and implantable devices with incorporating skirts or other elements of porous material. Examples of such other applications for devices of the present invention are illustrated in FIGS. 7 through 13.

Figure 7:
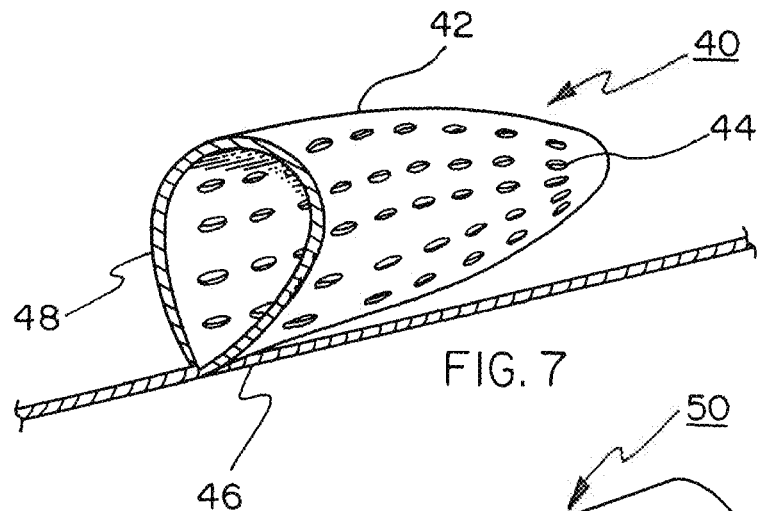
FIG. 7 is a three-quarter isometric view of an embolic filter of the present invention, including a frame and a porous membrane.

FIG. 7 illustrates one form of an embolic filter device 40 of the present invention. In this embodiment, the device 40 includes a porous membrane 42, having multiple macroscopic openings 44 therein, attached to a guidewire 46 by a frame 48. By treating the porous membrane 42 in the manner described above, the membrane will rapidly wet-out so as to allow clear ultrasonic imaging of the device 40 following deployment. Additionally, it is believed that rapid wet-out of the membrane may also provide improved filtration performance for the membrane 42.

Figure 8:
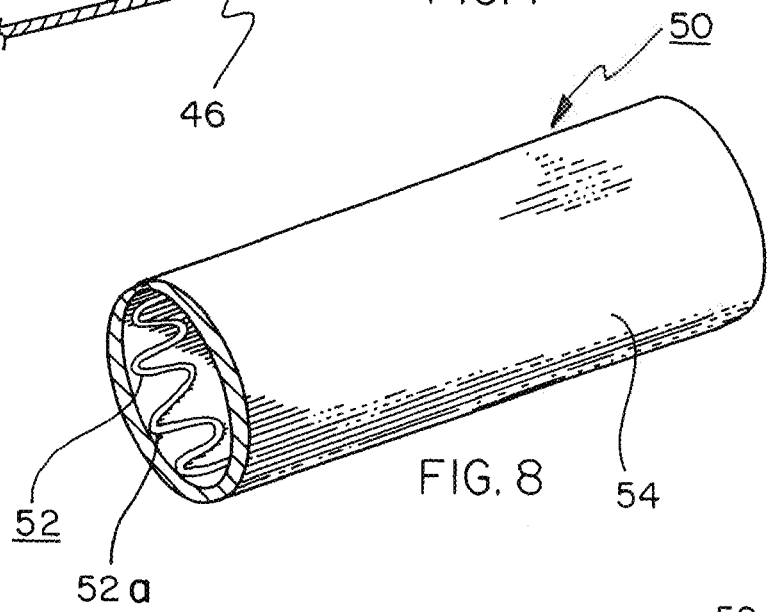
FIG. 8 is a three-quarter isometric view of a stent-graft of the present invention, including a frame and a porous membrane.
Figure 9:
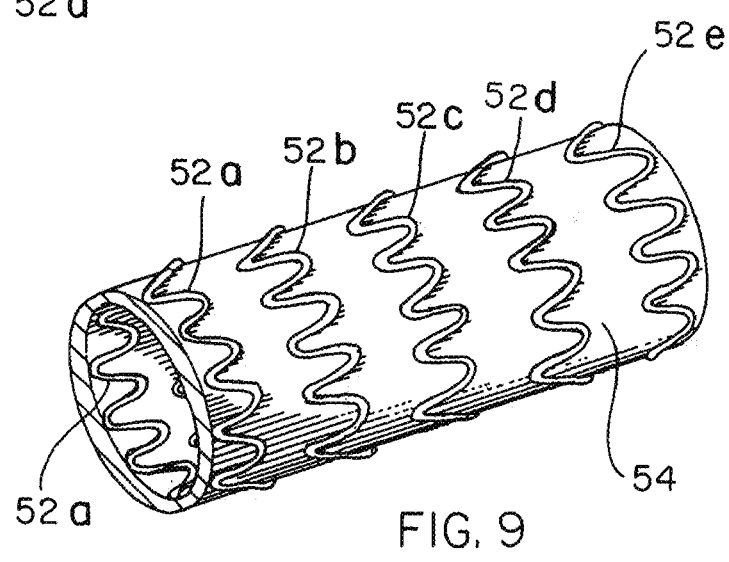
FIG. 9 is a three-quarter isometric view of the stent-graft of FIG. 8 following exposure to an aqueous liquid, the membrane component having been wetted-out so as to render visible the frame elements underneath.

FIGS. 8 and 9 illustrate a stent-graft device 50 of the present invention. In this embodiment, the device 50 includes a frame 52, comprising a series of undulating stent elements 52a, 52b, 52c, 52d, 52e, and a membrane 54 mounted around the outside of the frame 52. Although wet-out of many blood-deployed graft elements is not desired since such wet-out can lead to serum leakage, for some applications where such seepage is not an issue, a device of the present invention can be used to enhance visual and ultrasonic imaging. Even in instances where serum leakage may be undesirable, the benefits of the present invention can still be achieved by providing a barrier layer within the device to resist serum leakage. As is shown in FIG. 8, prior to exposure to an aqueous medium, the membrane 54 completely obscures the frame elements 52 mounted therein. Once exposed to blood or other aqueous liquid, as is shown in FIG. 9, the membrane 54 becomes translucent or even transparent so as to allow visualization of the frame 52 and the interior of the device. This kind of device is believed beneficial for certain stent-graft applications, such as carotid stenting, peripheral vascular stenting, or as a transjugular intrahepatic portacaval shunt (TIPS). This device may also be of use in the revision of the venous anastomosis of a vascular graft used for hemodialysis access, in coronary artery bypass graft revisions, or in stenting coronary arteries. Additionally, the rapid wet-out of the membrane may also provide additional benefits, such as presenting a better blood contact surface within the device, and allowing more rapid cell ingrowth into the device.

Figure 10:
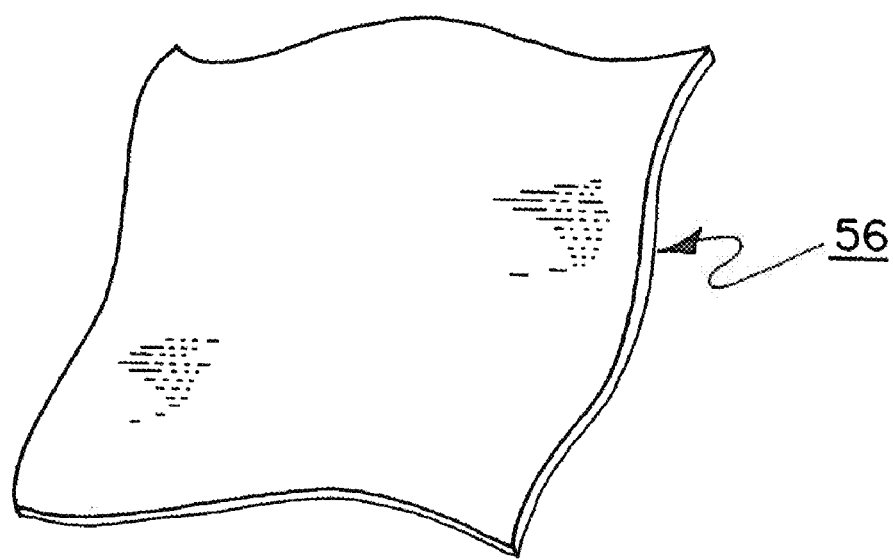
FIG. 10 is a three-quarter isometric view of a porous implantable membrane of the present invention.
Figure 11:
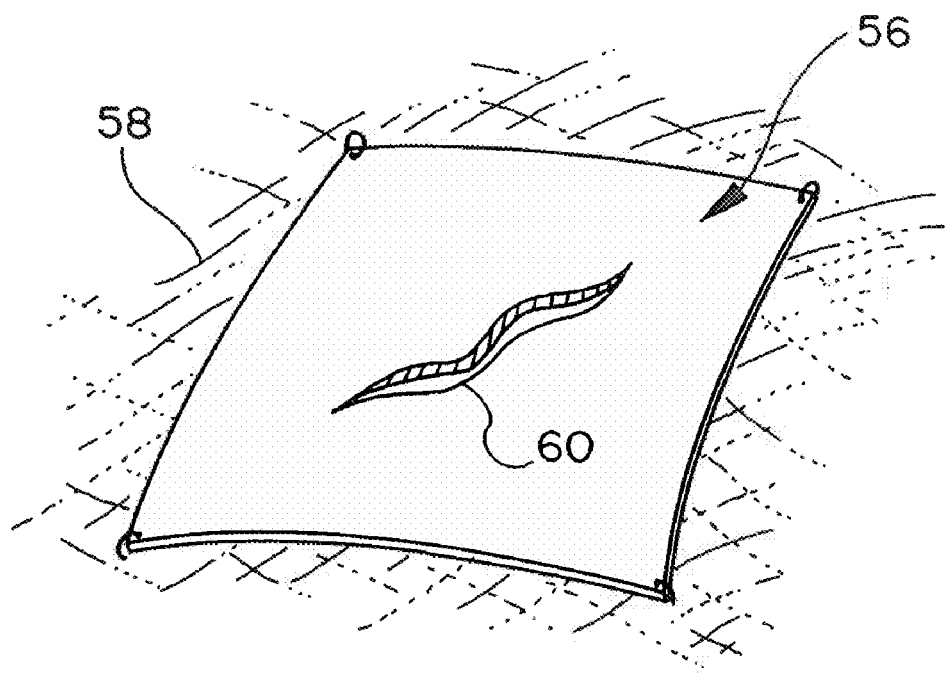
FIG. 11 is a three-quarter isometric view of the porous implantable membrane of FIG. 10 following initial implantation over a tissue defect, the membrane having been rendered transparent by contact with aqueous media at the surgical site.

Still another application for the present invention comprises an implantable sheet device 56 as illustrated in FIGS. 10 and 11. In this embodiment, the device 56 comprises a porous membrane, such as one constructed from expanded PTFE and commercially available from W. L. Gore & Associates, Inc., in a variety of forms such as those sold under the trademarks GORE-TEX®, PRECLUDE®, MYCROMESH®, or DUALMESH®. Although all of these membranes have been engineered for different implantation applications, each shares the common property of being constructed at least in part from a hydrophobic porous expanded PTFE material. This material is highly light reflective and can result in some glaring when implanted under bright surgical light in the surgical site. This may likewise be a problem when implanted endoscopically and the physician must view the surgical site through remote video imaging. For some such applications it is believed that allowing the membrane to be rapidly rendered translucent or transparent, as is shown in FIG. 11, may aid the physician in placing and anchoring the sheet in place. Additionally, as is also shown in FIG. 11, a translucent sheet 56 may also allow visualization of underlying tissue 58 and confirmation of proper sheet placement over areas requiring repair, such as a tissue tear 60. Again, additional benefits that a wetted-out sheet could provide may include improved blood or other body fluid contact, and/or improved tissue ingrowth.

In instances where serum leakage is undesirable, a barrier membrane can be placed within the device construct to prevent serum leakage. One such device is available from W.L. Gore & Associates, Inc., as the GORE-TEX® ACUSEAL Cardiovascular Patch. This device comprises two layers of expanded PTFE and a middle barrier layer of thermoplastic fluoropolymer elastomer. This middle barrier layer can serve in part as a support frame for the two layers of expanded PTFE. When the outer layers of expanded PTFE are treated with PVA, this embodiment of the invention is particularly useful as a surgical membrane for use in carotid artery endarterectomy repair, where it is desirable to check the patency of the repaired vessel immediately following the surgery using ultrasound.

As the term "membrane" is used herein it is intended to include any porous material that may be incorporated into an implantable device in any suitable shape and configuration. Suitable configurations contemplated by the present invention include sheets, tubes, fibers, rods, etc. Configurations may also include other shapes, such as the folded-over strips of material illustrated in the septal defect closure device of FIG. 1. The porous material may include any of, or any combination of, the following materials: expanded PTFE, polypropylene, polyolefin hollow fiber, polyvinylidene fluoride, PTFE, fluorinated ethylene propylene (FEP), hexafluoropropylene, polyethylene, polypropylene, polyamide (nylon), polyethyleneterephthalate, polyurethane, silicone rubber, polystyrene, polysulfone, polyester, polyhydroxyacid, polycarbonate, polyimide, polyamino acid, regenerated cellulose, or proteins, such as silk, wool, and leather. Particularly preferred for use with the present invention is a porous expanded PTFE material, such as that employed in various medical products available from W. L. Gore & Associates, Inc.

As the term "frame" is used herein it is intended to include any support structure that may be incorporated into or used with an implantable device. Suitable configurations may include defect closure frame configurations, any of a wide variety of stent frame configurations, filter frame configurations, occluder configurations, or any frame designed to aid in the positioning of a porous material in a body. Suitable materials include metals, such as stainless steel, nitinol, MP35N, titanium, or other metals used in biomedical applications; plastics, such as PTFE, expanded PTFE, polypropylene, fluorinated ethylene propylene, hexafluoropropylene, polyethylene, polypropylene, nylon, polyethyleneterephthalate, polyurethane, silicone rubber, polystyrene, polysulfone, polyester, polyhydroxyacids, polycarbonate, thermoplastic fluoropolymer elastomer, or other plastics used in biomedical applications; as well as other materials suitable for use in biomedical applications. The frame may be internal, external or both with respect to the porous membrane.

Without intending to limit the present invention to the specifics described hereinafter, the following examples illustrate how the present invention may be made and used.

Example 1

Process for Coating a Septal Occluder

A HELEX™ Septal Occluder (SO) is acquired from W. L. Gore & Associates, Inc., Flagstaff, Ariz. This device, illustrated in FIGS. 1 through 4, comprises a nitinol metal frame and a porous expanded PTFE sheet wrapped around the metal frame.

The entire SO is immersed in 100% isopropyl alcohol for 30 seconds. The SO is then transferred to a 2% PVA/DI Water solution for 30 minutes. The SO is rinsed in DI water for 10 minutes and then placed in a 2% glutaraldehyde/1% hydrochloric acid-DI water solution for 15 minutes. The SO is then rinsed in DI water for 15 minutes and allowed to air dry.

This final treated SO wetted-out rapidly when exposed to an aqueous solution, the membrane becoming completely translucent within 5 seconds after submersion in a water bath.

Example 2

Process for Coating Stent-Graft

A VIATORR™ Stent-Graft is acquired from W. L. Gore & Associates, Inc., Flagstaff, Ariz. This device, designed for establishing a shunt through a patient's liver in a transjugular intrahepatic portacaval shunt (T.I.P.S.) procedure, comprises a nitinol metal stent-element that is partially covered with a tubular expanded PTFE graft element.

The stent-graft is placed in 100% IPA for 30 seconds and then immediately transferred into a 2% PVA/DI Water solution for 20 minutes. The stent-graft is then transferred into a DI water rinse for 15 minutes. The stent-graft is then placed in the 2% glutaraldehyde/1% hydrochloric acid-DI water solution for 15 minutes. The stent-graft is then transferred into a final DI rinse for 15 minutes.

The final stent-graft device wet out rapidly when exposed to DI water, becoming completely translucent within 5 seconds after submersion in the water.

Example 3

Process for Coating Embolic Filter

The filtering membrane was made by laser perforating one layer of a thin (total thickness about 0.0005 cm (0.0002 in)) polytetrafluoroethylene (PTFE) membrane from W.L. Gore & Associates, Elkton, Md. A hole pattern of uniform size and spacing was created. The perforated membrane was then folded on itself and heat-sealed using a soldering iron to create a conical shape. The conical flat pattern was then trimmed with scissors, inverted, and mounted on a tapered mandrel.

The conical filter membrane was attached to a nitinol metal frame using a fluorinated ethylene propylene (FEP) powder coated adhesive (FEP 5101, available from E. I duPont de Nemours & Co., Wilmington, Del.) and localized heat application.

Following embolic filter construction, the embolic filter was placed in 100% IPA for 30 seconds. The device was then immediately transferred into a 2% PVA/DI Water solution for 20 minutes. Then the device was transferred into a DI water rinse for 15 minutes. Following the rinse, the device was placed in a 2% glutaraldehyde/1% hydrochloric acid-DI water solution for 15 minutes. The device was then transferred into a final DI rinse for 15 minutes.

Without the PVA treatment the device would not pass any fluid. After PVA treatment, the device was very effective at passing fluid while stopping the 100 micron and larger particles with over 98% efficiency.

Example 4

Process for Coating a Pericardial Membrane

A PRECLUDED® Pericardial Membrane (PCM) was acquired from W. L. Gore & Associates, Inc., Flagstaff, Ariz., and treated as follows. The PCM was immersed in IPA for 30 seconds. The PCM was immediately transferred into a 2% PVA/DI Water solution for 30 minutes. The PCM was transferred into a DI water rinse for 10 minutes. The PCM was placed in a 2% glutaraldehyde/1% hydrochloric acid-DI water solution for 15 minutes.

The PCM was then transferred into a final DI rinse for 15 minutes.

Example 5

Use of Pericardial Membrane in an Animal Model

The PCM made as described in Example 4, above, was implanted into an animal model. Immediately following implant the PCM material became visually transparent and presented no noticeable glare.

Example 6

Use of Septal Occluder in an Animal—Visualization by Ultrasound

An ultrasound machine (Sequoia C256, Acuson Corporation, Mountain View, Calif.) with an Intracardiac Probe (Acunav, Acuson Corporation, Mountain View, Calif.) was used to assess the clarity of visualization of the HELEX Septal Occluder treated according to Example 1. The treated device was immersed in heparinized saline and then deployed into a canine acutely. The edges of the device were clearly seen. The differences between the inventive device and a control are illustrated in FIGS. 5 and 6 and have been previously described.

Example 7

Testing for Hydroxyl Groups

This example describes an assay by which uniformity of coverage of devices with cross-linked polyvinyl alcohol (PVA) can be qualitatively assessed by visual inspection and quantitatively assessed by removal of the dye and spectrophotometric measurement of the dye concentration. The assay employs a blue dye, Cibachron Blue 3GA, which binds to free hydroxyl groups that are present on the surface of immobilized PVA. One molecule of Cibachron Blue binds to one free hydroxyl, so one can quantify free hydroxyl availability by removal of the attached dye with strong acid.

Binding of Cibachron Blue 3GA was accomplished using a modification of the method described in Hermanson, G. T., Mallia, A. K., and Smith, P. K., *Immobilized Affinity Ligand Techniques*, 1992, Academic Press, p. 176, as follows:

1. A piece of PVA-coated Septal Occluder made in accordance with Example 1 is cut, weighed and measured;
2. Add 10 ml deionized water to the membrane and heat to 60° C. in a tube block heater;
3. Add 0.1 gm of Cibachron Blue 3GA in 3 ml water, and heat at 60° C. for 30 min;
4. Add 1.5 gm NaCl and heat at 60° C. for 1 hr;
5. Raise the temperature to 80° C.;
6. Add 0.15 gm $Na_2CO_3$ and heat at 80° C. for 2 hr;
7. Cool, remove dye and rinse with water until no more color is removed.

Controls not treated with PVA are wetted with absolute ethanol, then water-rinsed prior to the above regimen. Any residual color on controls can be removed by a 15 min. treatment in absolute ethanol after water rinsing, and followed by more water rinses. Alcohol will not affect the dye on the PVA.

Removal of the dye for quantification is done according to a modification of the procedure of Clonis, Y. D., Goldfinch, M. J., and Lowe, C. R. Biochem. J. 197, 1981, 203-11, "The interaction of yeast hexokinase with Procion Green H-4G," as follows:

1. The stained PVA-coated membrane is cut into small pieces and placed in a vial containing 0.6 ml of 5N HCl. The vial is then heated at 60° C. for 3 hrs in a test tube block heater.
2. Then, 2.4 ml of 2.5 M sodium phosphate buffer, pH 7.4, is added, and the tubes are agitated for 5 min to extract the color from the membrane pieces.
3. The extract is removed, and the absorbances are read on a Varian DMS300 UV/VIS spectrophotometer at 620 nm.
4. The amount of dye in the extract is quantified from a standard curve constructed by preparing a series of Cibachron Blue solutions in the HCl/sodium phosphate mix ranging in concentration from 20 to 200 g/ml.
5. The membrane pieces from which the dye is extracted are washed in water. These pieces should now be white.

The results are expressed as μg Cibachron Blue/mg device. Four samples were tested according to the protocol above. The results were: 4.45+/−1.45 μg dye/mg Helex, N=4. The untreated (control) samples did not take up any dye.

Example 8

FTIR Test for Hydroxyl Groups

The degree of cross-linking of the layer may be assessed by Fourier Transform Infrared Spectroscopy (FTIR). For example, with FTIR the free hydroxyl groups of polyvinyl alcohol (PVA) are detectable before crosslinking at approximately 3349 $cm^{-1}$. After cross-linking, the peak shifts to approximately 3383 $cm^{-1}$ and decreases in height. As a positive internal control, an FTIR peak at approximately 2942 $cm^{-1}$ due to the $CH_2$ groups does not change position or height as a result of cross-linking. A shift in the hydroxyl group (—OH) peak position from approximately 3349 $cm^{-1}$ to approximately 3383 $cm^{-1}$ with a decrease in peak height is an indication of the amount of PVA that has become cross-linked in the formation of the first layer.

The detection of the broad hydroxyl peak at approximately 3383 $cm^{-1}$ was confirmed on a HELEX Septal Occluder made according to Example 1, using a Model 560ESP FTIR (NICOLET Corp., Madison, Wis.) and an ATR crystal apparatus (Zinc-Selenium 45 deg., Part #0050-603, SpectraTech, Stamford, Conn.). An untreated control HELEX Septal Occluder demonstrated no peak between 3000 and 3600 $cm^{-1}$.

Example 9

Evaluation of Tissue Ingrowth of Lame Hole GORE-TEX® MYCROMESH® Biomaterial and GORE-TEX® DualMesh Biomaterial Impregnated with PVA Six New Zealand White Rabbits were used in this study. Samples of Large Hole GORE-TEX® MYCROMESH® Biomaterial and GORE-TEX® DualMesh Biomaterial® were obtained from W.L. Gore & Associates, Inc. (Flagstaff, Ariz.). The samples were treated with PVA according to the method described in Example 4 to create hydrophilic membranes. Four samples were implanted in each of six animals. Two approximately 2.5 cm disks, one MYCROMESH biomaterial and one DUALMESH biomaterial were implanted subcutaneously on the rabbit dorsum. Two approximately 3.75 cm disks, one MYCROMESH biomaterial and one DUALMESH biomaterial were implanted intra-abdominally on the peritoneal wall in contact with viscera.

One side of both materials has a textured appearance. The MYCROMESH biomaterial was implanted with the textured side opposed to muscle, the DUALMESH biomaterial was implanted with the textured side adjacent to muscle. Animals were in-life for 7 and 30 days. There were 3 animals per in-life period.

Explant Observations

7 Day Explants: No adhesions were observed to both materials in the intra-abdominal regions. Both materials were generally covered by a thin translucent capsule within the subcutaneous tissue. The surrounding soft tissue was unremarkable.

30 Day Explants: No adhesions were observed to both materials. The surrounding soft tissue in the intra-abdominal region appeared unremarkable. A thin translucent capsule covered both implants in the subcutaneous region.

Histological Analysis

7 Day Explants: Large Hole GORE-TEX® MYCROMESH® Biomaterial: The tissue response was a minimal foreign-body reaction with mild inflammation consistent with wound healing. The periimplant membrane consisted of early granulation tissue containing numerous and scattered large and small blood vessels. The cellular components, at the interface, consisted of histiocytes and foreign body giant cells. The peripheral nerve bundles appeared unremarkable with mild degeneration consistent with wound healing. Numerous blood vessels were observed within the macropores. The neomesothelium dipped down and covered the macropores in the intraperitoneal region. Cellular migration into the interstices was extensive and scattered throughout the implants.

Polarized light microscopy revealed the nodes of the expanded PTFE to be aligned parallel and consistent through the entire implant. The fiber lengths appeared large. Occasionally, the implants appeared loosely adherent to the underlying muscle tissue.

GORE-TEX® DUALMESH Biomaterial: The microstructure appeared similar to the large hole MYCROMESH Biomaterial with consistent parallel aligned nodes with large fibril lengths. Cellular migration into the interstices was extensive and scattered with numerous red blood cells and histiocytes. The periimplant membrane consisted of granulation tissue with numerous blood vessels. There was no evidence of bacteria or calcification.

30 Day Explants: Large Hole MYCROMESH® Biomaterial: The periimplant membrane appeared to have a bland fibrocollagenous tissue with linearly aligned collagen fibers. The foreign-body tissue response was minimal. There was no evidence of inflammation in several of the implants. Cellular migration into the interstices was extensive with considerable collagen deposition. Blood vessels were numerous at the interface. The peripheral nerve bundles appeared unremarkable. Capillaries were observed within the interstices. Cellular migration was observed from both interfaces. There was no evidence of bacteria. A few microfoci of calcification were observed.

DUALMESH® Biomaterial: The periimplant membrane consisted of a bland fibrocollagenous tissue with aligned parallel collagen fibers to the interface. The neomesothelial-like membrane appeared mature. Blood vessels were numerous at the interface consisting predominantly of capillaries. Cellular migration into the interstices was extensive and often scattered. Collagen deposition was evident. Some of the sutures demonstrated occasional microfoci of calcification. The foreign-body tissue response was minimal. Several of the implants demonstrated no evidence of inflammation. There was no evidence of bacteria.

Conclusion

There was extensive cellular migration with collagen deposition into the interstices of both implants at the 30 day time frame. The migration of cells into both implants at the 7 day time frame was remarkable and considerable. The periimplant membrane appeared to consist of a bland fibrocollagenous tissue. Small blood vessels were numerous at the interface of both implants. The nerve bundles in the subcutaneous site, at the 7 day time frame, demonstrated degeneration consistent with wound healing, but appeared unremarkable at the 30 day time frame. Cellular ingrowth into the treated membrane spanned the entire membrane width (>500 um).

Cellular migration into the interstices of the large hole MYCROMESH® Biomaterial was evident from both interfaces. The foreign-body tissue response was minimal. There was no evidence of inflammation in many of the implants at the 30 day time frame. There was no evidence of bacteria in all implants for all time frames. Occasionally, microfoci of calcification was sparsely observed in both implants and in the sutures.

Example 10

Subcutaneous Study of PRECLUDE® Dura Membrane in a Rabbit Model

Six adult New Zealand White Rabbits were used in this study. Samples of PRECLUDE® Dura Substitute were obtained from W. L. Gore & Associates, Inc. (Flagstaff, Ariz.) and treated according to the method described in Example 4 to create hydrophilic membranes. Two surfactants, Dioctyl Sodium Sulfosuccinate (DSS) and Polyvinyl alcohol (PVA), were used to render the material immediately wettable with water or saline, allowing for vessel and tissue visibility during surgery, and to help in postoperative evaluations. Two, approximately 2.5 cm diameter disks were implanted subcutaneously on the dorsum of the rabbit. One device was treated with DSS and one with PVA. There were two in-life periods, of 7 days and 30 days, with 3 animals at each in-life time period.

Explant Observations

7 Day Explants: All of the implants appeared wet-out and intact. The implants were loosely adherent to the underlying muscle tissue. Occasional regions of hemorrhage were observed at the suture site. The implants were covered by a thin, translucent capsule along the anterior surface, toward the parietal region. Blood vessels were occasionally observed in the posterior region, along the muscle tissue.

30 Day Explants: All of the implants were generally encapsulated by a translucent to a slightly opaque capsule. Many of the implants appeared to be firmly to loosely adherent to the underlying muscle tissue. Suture sites still showed persistent brownish/reddish granular regions.

Histological Evaluation

7 Day Explants: A gradient effect was observed among all three materials. Consistently, the Dura Membrane treated with PVA revealed no adherence to the underlying soft tissue. The adipose tissue, at the interface, appeared benign. The foreign-body tissue response and histiocytic response were minimal.

The Dura Membrane implants treated with DSS demonstrated no adherence to the underlying muscle tissue. However, within the adipose tissue numerous foreign body giant cells and histiocytes were observed with a few vacuoles. This adipose tissue appeared mildly inflamed.

The Dura Membrane control demonstrated a marked inflammatory effect characterized by a zone of fibrinous regions as well as histiocytes and foreign body giant cells within the adipose tissue. The periprosthetic tissue was generally in close proximity to the Dura Membrane.

30 Day Explants: The PRECLUDE® Dura Membrane implants treated with PVA consistently revealed non-adherence to the underlying soft tissue. The periprosthetic tissue appeared bland. The underlying adipose tissue was unremarkable.

The Dura Membrane implants treated with DSS demonstrated close proximity of the periprosthetic tissue to the surface of the Dura Membrane. Occasional regions of focal attachment were observed along one surface of the Dura Membrane. Generally, mild inflammation with hypercellularity of the periprosthetic tissue was observed. Occasional foreign body giant cells and histiocytes were observed within the adipose tissue.

The Dura Membrane control implants consistently revealed close proximity of the periprosthetic tissue to both surfaces of the implants. Numerous regions of focal attachment of the periprosthetic tissue to the Dura Membrane were observed. Generally, inflammation with hypercellularity of the periprosthetic tissue was observed. Foreign body giant cells and histiocytes were observed within the adipose tissue. There was no evidence of bacteria or calcification at all time periods in all the implants.

Conclusion

The PRECLUDE® Dura Membrane treated with PVA demonstrated non-adherence of the periimplant membrane. The tissue response was bland.

The Dura Membrane treated with DSS demonstrated close proximity of the periimplant membrane with focal regions of attachment and mild inflammation of the adipose tissue.

The Dura Membrane control implants demonstrated an adverse tissue response. This was characterized by close apposition of the periimplant membrane to both surfaces. Numerous regions of focal tissue attachment and persistent inflammation of the adipose tissue were apparent.

Example 11

Treatment of Corneal Prostheses

Figure 12:
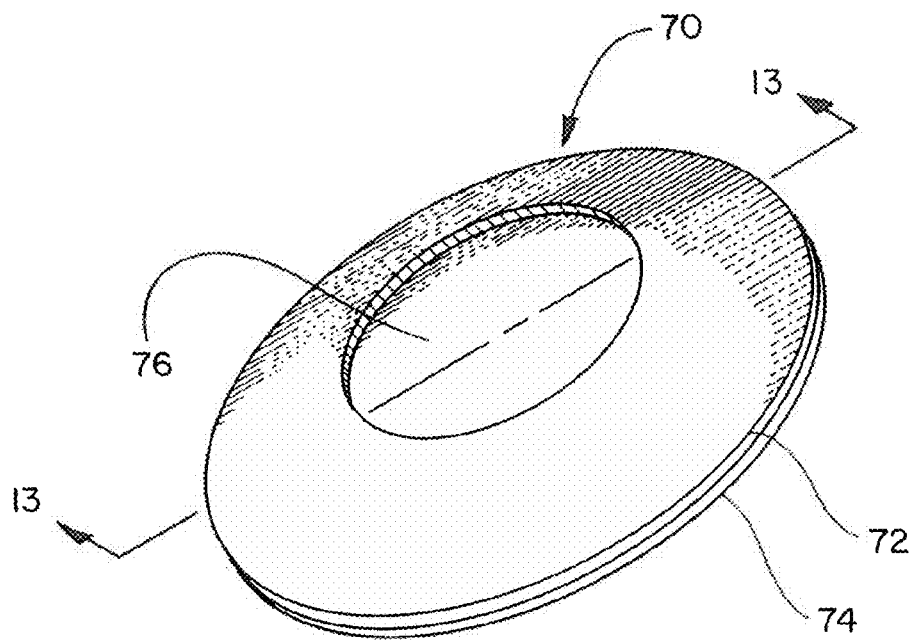
FIG. 12 is a three-quarter perspective view of another embodiment of the present invention comprising an artificial cornea having a porous membrane attached around a transparent lens member, said lens serving in part as the frame supporting the porous membrane.
Figure 13:
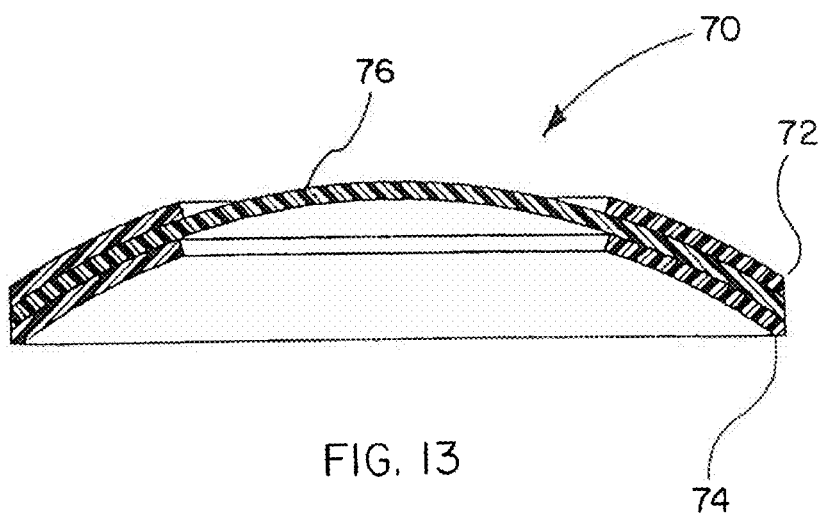
FIG. 13 is a cross-section view along line 13-13 of FIG. 12.

Corneal prostheses (or "keratoprostheses") were made, treated with PVA, implanted and evaluated after explant. Shown In FIG. 12 is an isometric view of an implantable corneal prosthesis. Shown is a keratoprosthesis 70 having expanded PTFE peripheral skirts 72, 74 attached to a fluoropolymer corneal substitute 76. The expanded PTFE skirts were treated with PVA in accordance with the procedure described in Example 4. Shown in FIG. 13 is a cross-sectional view of an implantable keratoprosthesis 70, showing a first expanded PTFE skirt layer 72, a second expanded PTFE skirt layer 74 and an polymeric corneal substitute layer 76. The corneal substitute layer 76 was shaped to conform to surrounding native tissue and had a thickness and flexibility suitable for long term ocular implantation. The corneal substitute layer 76 provided an "internal" support frame for the expanded PTFE membranes.

Keratoprosthesis 70 was produced by providing a sheet of expanded PTFE, commercially available from W. L. Gore & Associates, Inc., as GORE-TEX® Soft Tissue Patch. The 2 mm (0.04") thick expanded PTFE sheet was split into sheets approximately 0.15 mm (0.006") thick. Holes having diameters of about 5.5 mm (0.22") were laser cut into the sheets. A stacked assembly was then prepared for a first lamination process, which bonded a thermoplastic fluoropolymer elastomer to the laser cut sheet. The stacked assembly was formed (from the top down) by aligning the following layers: a first aluminum plate about 30 mm (0.12") thick, a sheet of KAPTON®, high temperature plastic about 0.05 mm (0.002") thick available from E.I. duPont de Nemours, Wilmington Del., a sheet of 2 mm thick GORE-TEX® Soft Tissue Patch, a second sheet of KAPTON, a layer of thermoplastic fluoropolymer elastomer about 0.2 mm (0.008") thick, the laser cut expanded PTFE sheet, a third sheet of KAPTON, a second sheet of 2 mm thick GORE-TEX® Soft Tissue Patch, a fourth layer of KAPTON and a second aluminum plate. All layers were about 10 cm (4"0) square. This stacked assembly was placed into a heated platen press and laminated at about 200° C., under about 0.03 MPa (5 psi) for about 2 minutes. This first lamination process bonded the thermoplastic fluoropolymer elastomer to the first 0.15 mm thick expanded PTFE sheet with the laser cut holes.

A second sheet of the 0.15 mm thick expanded PTFE with laser cut holes was then aligned to and bonded to the thermoplastic fluoropolymer elastomer. A stacked assembly was prepared for a second lamination process which bonded the thermoplastic fluoropolymer elastomer to the second laser cut sheet. The stacked assembly was formed (from the top down) by aligning the following layers: a first aluminum plate about 30 mm (0.12") thick, a sheet of KAPTON, a sheet of 2 mm thick GORE-TEX® Soft Tissue Patch, a second sheet of KAPTON, a sheet of the 0.15 mm thick expanded PTFE with laser cut holes, the bonded thermoplastic fluoropolymer elastomer/first laser cut expanded PTFE sheet, a third sheet of KAPTON, a second sheet of 2 mm thick GORE-TEX® Soft Tissue Patch, a fourth layer of KAPTON, and a second aluminum plate. All layers were about 10 cm (4") square. The laser cut holes in the first and second sheets were concentrically aligned to each other. This stacked assembly was placed into a heated platen press and laminated at about 200° C., under about 0.03 MPa (5 psi) for about 2 minutes. This second lamination process bonded the thermoplastic fluoropolymer elastomer to the second 0.15 mm thick expanded PTFE sheet with the laser cut holes, resulting in a three layer laminate as depicted in FIG. 13.

The three layered laminate was then aligned onto a laser. Disks approximately 9.7 mm (0.39") were concentrically cut relative to the existing 5.5 mm holes. The disks were then formed into the convex shape by compression forming and then heating to retain the final shape. The resulting keratoprosthesis is depicted in FIGS. 12 and 13.

The keratoprosthesis was then treated with PVA using the following process:

1) The keratoprosthesis was placed into a 60 ml syringe containing about 30 ml of 100% isopropyl alcohol. The air was expelled from the syringe. The syringe plunger was then partially withdrawn with the syringe port plugged, forming a partial vacuum within the syringe. The vacuum was maintained for about 15 seconds and then the plunger was allowed to relax. This vacuum application was repeated five more times. The vacuum application forced the residual air from the porous expanded PTFE, allowing the alcohol to fully penetrate.
2) The keratoprosthesis was then soaked in a 2% PVA/DI water solution for about 2 hours, stirring at about 45 minute intervals.
3) The keratoprosthesis was then rinsed in DI water for about 30 minutes with occasional stirring.
4) The keratoprosthesis was then placed in a 2% glutaraldehyde/1% hydrochloric acid-DI water solution for about 1.5 hours, with occasional stirring.
5) The keratoprosthesis was then rinsed in DI water for about 30 minutes with occasional stirring.
6) The treated keratoprosthesis was then sterilized prior to implantation.

A study was performed to evaluate the healing process and tissue response of keratoprosthesis prototypes in a New Zealand White Rabbit. PVA treated e-PTFE keratoprostheses were compared with untreated expanded PTFE prototypes in four animals each. The groups were examined by gross and histological analysis after an implant period of 90 days.

Prototypes treated with PVA had superior performance compared to their untreated counterparts. One prototype in the untreated group failed at 68 days. Two of the four of the untreated group had skirt lifting, indicating poor device anchorage. Additional gross observations of the untreated prototypes included patchy areas of wet-out expanded PTFE compared with complete wetting-out of the expanded PTFE in the PVA treated group. In addition, there was glistening on the anterior expanded PTFE surface of the PVA group, confirmed to be corneal epithelial attachment with histology. This phenomenon did not appear in the untreated group. Tissue attachment in both groups stopped at the expanded PTFE/thermoplastic elastomer junction.

While particular embodiments of the present invention have been illustrated and described herein, the present invention should not be limited to such illustrations and descriptions. It should be apparent that changes and modifications may be incorporated and embodied as part of the present invention within the scope of the following claims.

The invention claimed is:

1. A method of visualizing a medical device during implantation thereof with ultrasonic imaging, said method comprising:
   (a) providing a medical device having at least a portion thereof made of an opaque porous expanded polytetrafluoroethylene material and at least one dried, covalently cross-linked, hydrophilic polymeric material placed in pores of said porous expanded polytetrafluoroethylene material;
   (b) exposing said medical device to an aqueous medium in vivo;
   (c) permitting said aqueous medium to contact said hydrophilic polymeric material in pores of said porous expanded polytetrafluoroethylene material;
   (d) visualizing said medical device with ultrasonic imaging in the presence of said aqueous medium; and
   (e) observing at least a portion of said opaque porous expanded polvtetrafluoroethylene material becoming translucent or transparent during said ultrasonic imaging.

2. The method of claim 1 wherein said aqueous medium is blood.

3. The method of claim 1, wherein the visualizing takes about thirty seconds or less.

4. The method of claim 1, wherein the visualizing takes about ten to five seconds or less.

5. The method of claim 1, wherein the visualizing is substantially instantaneous.

6. The method of claim 1, wherein the hydrophilic polymeric material is selected from the group consisting of polyvinyl alcohol, polyethylene glycol, polypropylene glycol, dextran, agarose, alginate, polyacrylamide, polyglycidol, poly(vinyl alcohol-co-ethylene), poly(ethyleneglycol-co-propyleneglycol), poly(vinyl acetate-co-vinyl alcohol), poly(tetrafluoroethylene co-vinyl alcohol), poly(acrylonitrile-co-acrylamide), poly(acrylonitrile-co-acryl-ic acid-co-acrylamide), polyacrylic acid, poly-lysine, polyethyleneimine, polyvinyl pyrrolidone, polyhydroxyethylmethacrylate, polysulfone, and combinations thereof.

7. The method of claim 1, wherein the hydrophilic polymeric material is cross-linked with a cross-linking agent comprising compounds having at least two chemically functional groups selected from the group consisting of homofunctional, heterofunctional, and combinations thereof.

8. The method of claim 1, wherein the hydrophilic polymeric material is cross-linked with a cross-linking agent selected from the group consisting of aldehydes, epoxides, acyl halides, aryl halides, isocyanates, amines, anhydrides, acids, alcohols, haloacetals, arylcarbonates, thiols, esters, imides, vinyls, azides, nitros, peroxides, sulfones, maleimides and combinations thereof.

* * * * *